United States Patent [19]

Lazzara

[11] 3,996,476
[45] Dec. 7, 1976

[54] LOW NOISE PHOTOELECTRIC DETECTOR APPARATUS

[75] Inventor: Anthony Ross Lazzara, Portola Valley, Calif.

[73] Assignee: Scientific Technology Incorporated, Mountain View, Calif.

[22] Filed: Sept. 10, 1975

[21] Appl. No.: 611,871

[52] U.S. Cl. .............................. 250/563; 250/574; 250/208; 250/553; 250/552; 250/227

[51] Int. Cl.² ....................................... G01N 21/32

[58] Field of Search .......... 250/563, 574, 566, 227, 250/208, 211 J, 552, 553, 568

[56] References Cited

UNITED STATES PATENTS

| | | | |
|---|---|---|---|
| 3,555,532 | 1/1971 | White et al. | 250/574 |
| 3,561,846 | 2/1971 | Kingsland | 250/566 |
| 3,819,938 | 6/1974 | Kornrumpf et al. | 250/553 |
| 3,892,974 | 7/1975 | Elletson et al. | 250/568 |

Primary Examiner—Alfred E. Smith
Assistant Examiner—David K. Moore

[57] ABSTRACT

A photoelectric sensor includes a photodetector, a lens, and a light source all mounted within a framework for holding the lens with the photodetector and light source located on the central axis of the lens. The photodetector is positioned on the rear side of the lens within the framework at approximately the lens focal point. The light source is positioned to emit light away from the front side of the lens. Structure in the form of an opaque collar is provided for mounting the light source relative to the lens to prevent impingement of spurious light from the light source upon the lens. An object positioned in front of the lens intercepts the emitted light from the light source and reflects it back toward the lens, whereupon it is directed to the photodetector. A signal indicative of the presence of the object is provided by the photodetector responsive to the reflected light.

7 Claims, 8 Drawing Figures

LOW NOISE PHOTOELECTRIC DETECTOR APPARATUS

BACKGROUND OF THE INVENTION

This invention relates to a photoelectric detection apparatus with coaxial light emission and reception and more particularly to such a photoelectric detector for providing a low noise output signal.

Available photoelectric detection devices include a photosensor and a light emitting source both located on the axis of a lens for focusing received light on the photodetector. The light source is positioned to emit light in a direction forward of the lens, whereupon the emitted light may be reflected by an object passing in front of the lens. The reflected light is received by the lens and focused upon the photodetector for providing an output signal indicative of the presence of the object in front of the lens. Difficulty arises in interpreting the output signal as indicative of an object's presence due to the noise created in the output signal by spurious light from the light source which enters the lens directly from the light source. Internal reflection of light from the light source may also be transmitted to the photodetector further causing spurious output signal and masking the desired output signal. There is therefore, a need for a photoelectric sensing device which eliminates the major sources of noise in the output signal, and which thereby provides for a finer sensitivity to objects which are to be detected.

SUMMARY AND OBJECTS OF THE INVENTION

The low noise photoelectric sensing apparatus disclosed herein includes a framework having a lens mounted therein having a front and a rear side and a central axis passing therethrough. A lens focal point is located on the central axis toward the rear side of the lens and a photodetector is mounted in the framework approximately at the focal point. A light source is mounted on the central axis positioned toward the front of the lens for producing light which is emitted away from the forward side of the lens. Means are provided for cooperation with the light source which shields the lens from the light source so that spurious light from the light source will be prevented from entering the lens. In this manner the output signal from the photodetector is maintained free of noise which might otherwise be generated due to spurious light from the light source being focused on the photodetector by the lens.

In general it is an object of the present invention to provide a photoelectric sensing device which provides a low noise output signal.

It is another object of the present invention to provide a photoelectric sensing device which detects the presense of a plurality of objects simultaneously.

It is another object of the present invention to provide a photoelectric sensing device in which coaxial light emission and photodetection is obtained without cross-talk between the emitted light and the photodetector.

Additional objects and features of the invention will appear from the following description in which the preferred embodiments have been set forth in detail in conjunction with the accompanying drawings.

BRIEF DESCRIPTION OF THE DRAWINGS

FIG. 4b is a front elevation view of the embodiment of FIG. 4a.

DESCRIPTION OF THE PREFERRED EMBODIMENTS

Figure 1:
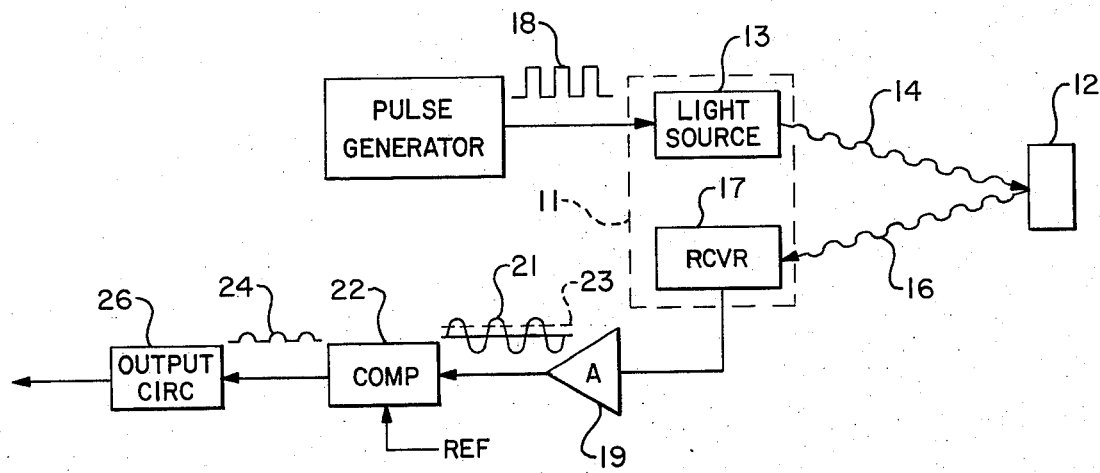
FIG. 1 shows a prior art photodetection system utilizing the disclosed photoelectric sensing apparatus.

Referring to FIG. 1 a proximity sensing system is shown including a photoelectric sensing device or optical assembly 11 together with an associated reflecting object 12. The remainder of FIG. 1 shows a block form the associated electrical circuits used in conjunction with the optical assembly 11 for driving a light source 13. Light source 13 emits light energy 14, which strikes reflecting object 12 causing reflected light energy 16 to be directed toward a receiver 17. Receiver 17 is in the nature of a photodetecting device and provides an output signal which may be amplified, compared and connected to an output circuit as shown.

A general desrition of one photoelectric sensing device as contained in U.S. Pat. No. 3,774,039 follows. Light source 13 may be a light emitting diode which is driven by a pulse generator which includes an amplifier and an oscillator. The amplifier is modulated by an input signal from the oscillator. The oscillator provides a square wave output signal which serves to turn the amplifier on and off thereby providing an amplifier square wave signal such as illustrating at 18 having a 50 percent duty cycle. This serves to turn on and off the light emitting diode 13 at a frequency corresponding to the frequency of the contained oscillator. Thus the light emitted by light emitting diode 13 is in the form of light pulses which travel outwardly therefrom to impinge upon objects such as reflecting object 12. As a result, diffused light reflected by object 12, or light from a reflector positioned as is object 12, is picked up by receiver 17. A detector in receiver 17 is excited to provide an output signal which is connected to the input of an amplifier 19 for producing an output signal 21 therefrom. The amplified output signal 21 is connected to the input of a comparator 22 which also receives a reference voltage. The reference voltage is shown at 23. Comparator 22 serves to pass only that portion of signal 21 which has an amplitude exceeding the reference voltage 23, whereby the output of the comparator 22 is a series of pulses 24. Pulses 24 are applied to an output circuit 26 which in turn provides an output signal which may be employed to drive associated relays, circuits or other apparatus.

Figure 2:
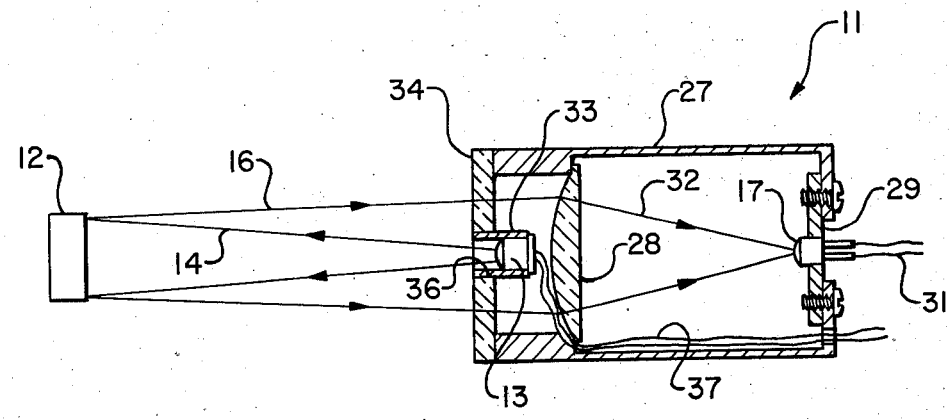
FIG. 2 is a side elevation sectional view of one embodiment of the photoelectric sensing apparatus.

FIG. 2 shows one embodiment of optical assembly 11 which includes a case or framework 27 having an internally mounted lens 28. Lens 28 has, in this embodiment, a convex front side and a planar rear side and may be held in place inside case 27 by a retainer (not shown) or an adhesive. Receiver 17 is represented by a photosensitive detector mounted in a plate 29 fastened to the rear end of case 27. Photosensitive detector 17 provides an output signal conducted through electrical leads 31 which is responsive to light energy 32 focused by lens 28 to impinge upon detector 17. Light source 13 is represented by a light emitting diode (LED) which is positioned forward of the front side of lens 28 and mounted in an opaque collar 33. A front protective lens 34 is mounted on the forward portion of case 27 and has a centrally located hole 36 therethrough. Hole 36 is formed to accept opaque collar 33 as shown, thereby mounting light source 13 on the central axis of lens 28. Electrical leads 37 are seen for connecting the LED excitation signal 18 to light source 13.

The embodiment of FIG. 2 functions as follows. LED 13 is excited by applying square wave 18 to leads 37 whereby LED 13 emits light energy 14 away from lens 28. Light energy 14 impinges upon reflecting object 12 causing reflected light energy 16 to return toward optical assembly 11 and to pass through protective lens 34. Reflected light energy 16 impinges upon lens 28 and is focused as light energy 32 to impinge upon photoelectric device 17, thereby providing an output signal in electrical leads 31. Opaque collar 33, in which LED 13 is mounted, prevents spurious emitted light energy 14 from impinging upon the back side of front protective lens 34 which might thereby be reflected to impinge upon lens 28 to cause unwanted output signal, or noise, in the output signal from photoelectric device 17. In this fashion output signal noise is reduced in an assembly with coaxial light source and photoelectric detection device which are located on opposite sides of a lens for focusing reflected light on the photoelectric detection device.

Figure 3:
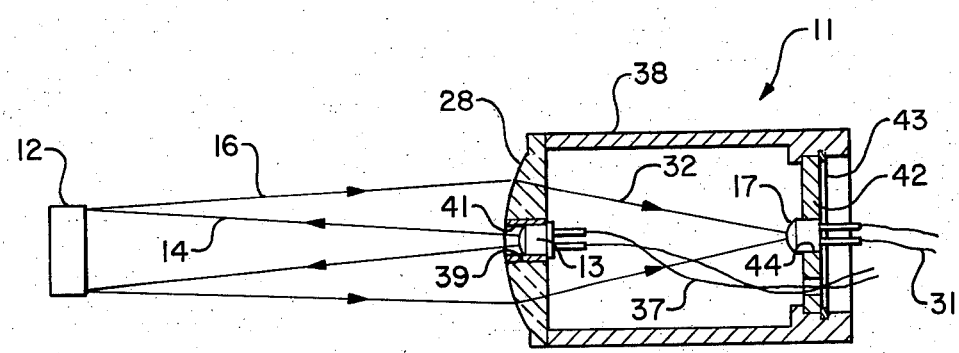
FIG. 3 is a side elevation sectional view of another embodiment of the photoelectric sensing apparatus.

FIG. 3 shows another embodiment of the present invention having a case or framework 38 of a different configuration than that of FIG. 2. Lens 28 is positioned on the front portion of case 38 by some convenient means such as an adhesive. Lens 28 has a centrally located hole 39. An opaque collar 41 is formed to fit within holes 39. Opaque collar 41 is also formed to receiver light source 13 to provide mounting therefor. A rear plate 42 is formed to be retained in case 38 by some means such as snap ring 43. Rear plate 42 has a centrally located hole 44 for mounting photoelectric device 17 therein.

It may be seen from FIG. 3 that light source 13 and photoelectric detector 17 are coaxially positioned on the central axis of lens 28. Photoelectric detector 17 is positioned at approximately the focal point of lens 28, whereby focused light energy 32 impinges thereupon for producing an output signal therefrom. LED 13 is shielded from lens 28 so that spurious emitted light energy 14 is blocked from entering lens 28 directly from LED 13. Emitter light energy 14 travels away from lens 38 to be reflected by reflecting object 12 in the form of reflected light energy 16 to impinge upon lens 28 as described above. Once again noise in the output signal produced by photoelectric detector 17 is reduced by prevention of "cross talk" between LED 13 and photoelectric detector 17.

Figure 4A:
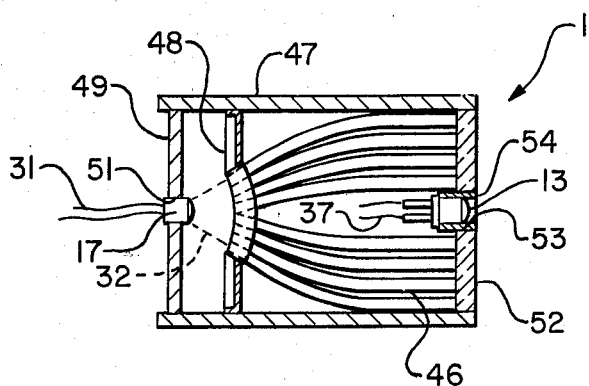
FIG. 4a is a side elevation sectional of an additional embodiment of the photoelectric sensing apparatus.

FIG. 4a shows another embodiment of the disclosed invention in which lens 28 is replaced by fiber-optics bundle 46. Light source 13 is positioned in the center of fiber-optics bundle 46, all of which is enclosed in another case or framework 47 configuration. Fiber-optics bundle 46 is shaped at the rear end thereof by means of a support 48 retained within the case 47 for directing light energy 32, to be focused upon photoelectric detector 17. A rear plate 49 is provided for retention in case 47 having a centrally located aperture 51 for receiving photoelectric detector 17. A front protective lens 52 is retained in the front portion of case 47 having a hole 53 centrally located therein. An opaque collar 54 is formed to fit in hole 53, and is also configured to receive LED 13 for mounting thereof.

Figure 4B:
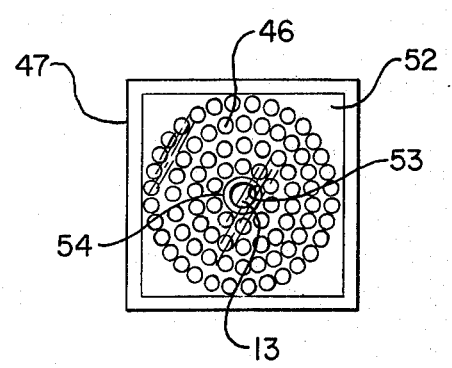

FIGS. 4a and 4b describe an embodiment of the present invention which functions as follows. LED 13 and photoelectric device 17 are coaxially mounted within case 47 on the central axis through the lens provided by fiber-optics bundle 46. LED 13 emits light energy in a forward direction away from front protective lens 52. The emitted light energy may strike an object in front of protective lens 52, thereby reflecting light energy back toward optical assembly 11. The reflected light energy passed through protective lens 52 into fiber-optics bundle 46 which is shaped at the rear end thereof by holder 48 to direct light energy 52 passing therethrough to impinge upon photoelectric device 17. In a manner such as that described above, photoelectric device 17 provides an output signal in leads 31 for use as previously described.

Figure 5:
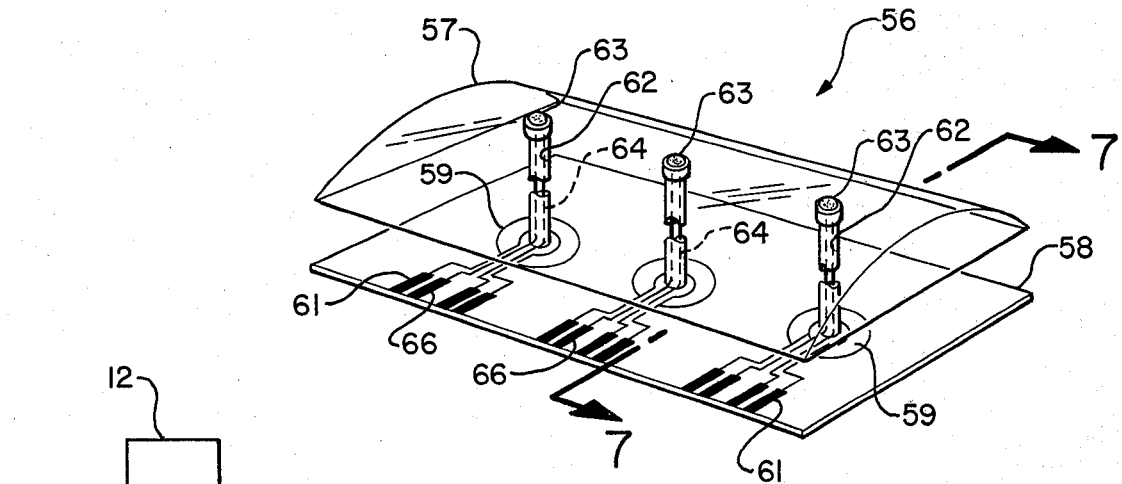
FIG. 5 is an isometric view of a plural element photoelectric sensing apparatus.

Reference is now made to FIG. 5. An array of optical assemblies 56 is shown wherein a lens 57 is depicted as spaced from a substrate 58. In the actual assembly the back side of lens 57 is coterminous with the surface of substrate 58 seen in FIG. 5. A plurality of photoelectric detectors 59 are positioned in spaced realtionship on substrate 58. Leads 61 are formed adhering to substrate 58. A plurality of apertures 62 are formed in lens 57 having spacing equal to the spacing between photoelectric detectors 59 on substrate 58. In this fashion apertures 62 overlie the pattern of detectors 59. A plurality of light sources 63 are provided having leads 64 extending through apertures 62 and connected to a plurality of electrical leads 66 attached to substrate 58.

Figure 7:
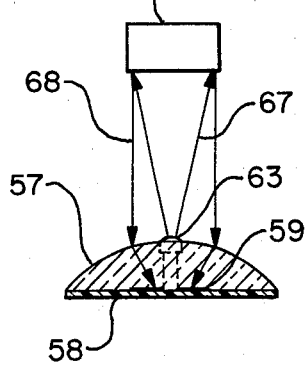
FIG. 7 is a sectional view along the lines 7—7 of FIG. 5.

Reference is made to FIG. 7 for the functional description of FIG. 5. Light source 63, which may be LED's, are seen to be positioned forward of the convex surface of lens 57 for emitting light energy 67 away fron lens 57. Emitted light 67 impinges upon reflecting object 12, causing reflected light 68 to approach the front surface of lens 57. Reflected light energy 68 is focused by lens 57 to impinge upon photoelectric detetors 59 on the surface of substrate 58. Since the emitted light energy 67 is produced forward of the convex surface of lens 57, there is no opportunity for spurious emitted light 67 to be directed toward photoelectric detectors 59 by refraction through lens 57. Consequently a low noise output signal from photoelectric detectors 59 is obtained.

Figure 6:
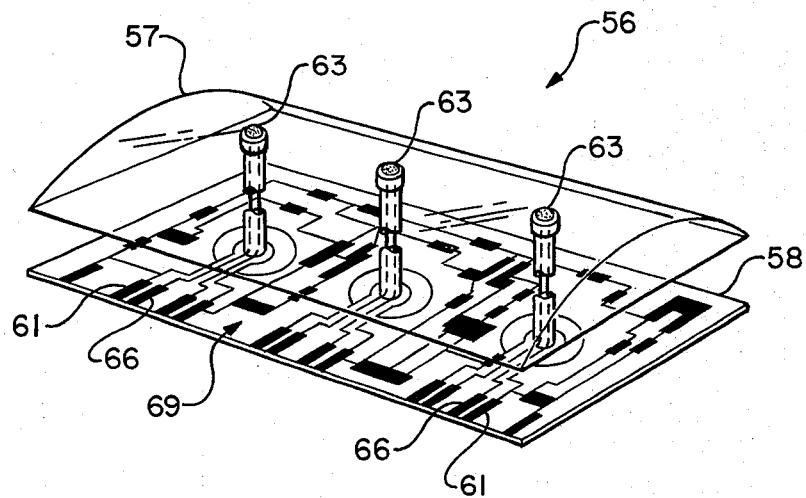
FIG. 6 is an isometric view of another embodiment of the plural photoelectric sensing apparatus.

FIG. 6 shows the embodiment of FIG. 5 together with additional circuit means 69 attached to the surface of substrate 58 for providing the associated pulse generation, amplification, comparator and output circuit functions described in FIG. 1 above. The remainder of the embodiment of FIG. 6 is as described for FIG. 5 above. The embodiments of FIGS. 5 and 6 are useful for obtaining signals indicative of the progress of a reflecting object 12 passing along the line of photoelectric detectors 59. These embodiments are also useful for detecting the passage of a plurality of reflecting objects 12 passing transverse to the line of photoelectric detectors 59. A further use for the embodiments of FIGS. 5 and 6 resides in the detection of varying heights of objects passing in front thereof along the line transversed to the line of photoelectric detectors 59. Furthermore the output from the photoelectric detectors 59 is free of noise which would be generated by spurious emitted light energy 67 is light sources 63 were positioned in back of the convex face of lens 57.

A low noise photoelectric sensing apparatus has been disclosed which eliminates output signal noise due to cross-talk between the light source and the photodetection device. The noise elimination is accomplished by means of optical blocking or by means of light source positioning relative to the focusing lens for the photoelectric device, or by a combination of both.

What is claimed is:

1. A low noise photoelectric sensing apparatus comprising a framework, a lens mounted in one end of said framework for focusing light impinging thereupon at a focal point located on the rear side of said lens on a central axis passing therethrough, said lens having a front side exposed to the exterior of said framework and having a central hole therein,
   a photodetector mounted in said framework on said central axis positioned toward the rear of said lens for receiving the focused light and providing an output signal related thereto,
   a light source mounted on said central axis positioned toward the front of said lens for emitting light away from said lens,
   an opaque collar formed to fit in said central hole for shielding said lens from said emitted light to reduce noise in said output signal resulting from spurious light from said light source impinging on said photodetector, said lens serving to receive emitted light only after reflection from objects in front of said lens, whereby said output signal provides a low noise indication thereof.

2. A low noise photoelectric sensing apparatus as in claim 1 wherein said lens comprises a bundle of fiberoptics.

3. A low noise photoelectric sensing apparatus as in claim 1 wherein said framework comprises a substrate, together with a plurality of additional photodetectors positioned on said substrate, said lens being mounted overlying said photodetector and additional photodetectors, said additional photodetectors producing a plurality of additional output signals, a plurality of additional light sources, one for each additional photodetector, said light source and additional light sources positioned on the front side of said lens, whereby emitted light from said light source and additional light sources is prevented from entering said lens.

4. A low noise photoelectric sensing apparatus as in claim 3 together with means mounted on said substrate for energizing said light source and additional light sources, means for receiving said output signal and additional output signals mounted on said substrate, said last named means providing an indication of reflecting surfaces passing in front of said lens.

5. A low noise photoelectric sensing apparatus comprising a supporting framework,
   a lens mounted in said framework having a front side, a rear wide, a central axis, and a focal point on the rear side of said lens,
   a photodetector mounted in said framework substantiallly at said focal point, for producing an output signal responsive to light impinging thereupon,
   a light source positioned on the front side of said lens, disposed to emit light away from said lens,
   an outer protective mounted in said framework on the front side of said lens, said outer protective lens having a hole therethrough on said central axis, and an opaque collar formed to fit in said hole and to receive said light source.

6. A low noise photoelectric sensing apparatus comprising a substrate,
   a plurality of photodetectors mounted in alignment on said substrate and producing a plurality of output signals when exposed to light of predetermined intensity,
   a lens overlying said substrate and photodetectors for focusing light impinging thereupon onto said photodetectors, said lens having
   a plurality of through holes, one for each photodetector and in alignment therewith,
   a plurality of light sources for emittng light and having electrical connections extending through said plurality of holes and positioned one each in front of said lens overlying each of said holes, and means on said substrate for providing electrical access to said light source electrical connections and said photodetectors, whereby objects passing in front of said lens reflect said emitted light toward said lens for focusing on said photodetectors for indicating object presence.

7. A low noise photoelectric sensing apparatus as in claim 6 together with
   means for energizing said plurality of light sources mounted on said substrate,
   means for receiving said plurality of output signals, said last named means being mounted on said substrate and providing a predetermined signal form for indication of size of the objects reflecting emitted light.

* * * * *